United States Patent
Atwood et al.

(10) Patent No.: US 6,586,600 B2
(45) Date of Patent: Jul. 1, 2003

(54) MULTIDENTATE SULFUR-CONTAINING LIGANDS

(75) Inventors: David A. Atwood, Lexington, KY (US); Brock S. Howerton, Lexington, KY (US); Matthew Matlock, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 23 days.

(21) Appl. No.: 09/730,622

(22) Filed: Dec. 6, 2000

(65) Prior Publication Data

US 2002/0100732 A1 Aug. 1, 2002

(51) Int. Cl.[7] ............... C07D 213/46; C07C 237/30; C02F 1/00
(52) U.S. Cl. ............. 546/323; 564/156; 546/6; 210/638; 210/688
(58) Field of Search ............. 546/323, 6; 564/156; 210/688, 638

(56) References Cited

U.S. PATENT DOCUMENTS

| | | | |
|---|---|---|---|
| 4,039,446 A | | 8/1977 | Ban et al. |
| 4,281,086 A | | 7/1981 | Gaul, Jr. et al. |
| 4,433,154 A | * | 2/1984 | Hirai ............ 548/195 |
| 4,508,838 A | | 4/1985 | Buckl |
| 4,969,995 A | | 11/1990 | Jackson et al. |
| 5,073,575 A | | 12/1991 | Blanch et al. |
| 5,173,470 A | | 12/1992 | Bruening et al. |
| 5,200,473 A | | 4/1993 | Jeanneret-Gris |
| 5,766,478 A | | 6/1998 | Smith et al. |

* cited by examiner

*Primary Examiner*—Charanjit S. Aulakh
(74) *Attorney, Agent, or Firm*—King & Schickli, PLLC

(57) ABSTRACT

Novel sulfur-containing ligands for binding of heavy metals are disclosed. The ligands incorporate a central ring structure and pendant alkyl-thiol chains. The ligands are of the general structure:

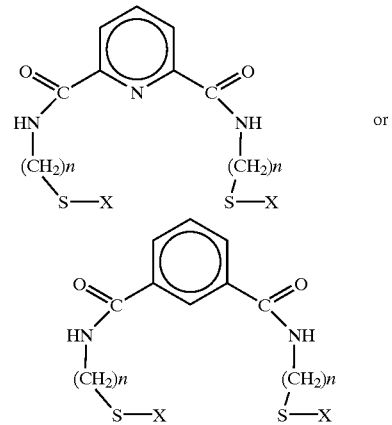

where n is an integer from 1–4, and X is selected from the group consisting of hydrogen, lithium, sodium, potassium, rubidium, cesium, and francium. The ligands of the present invention are suitable for binding any metal in or capable of being placed in a positive oxidation state, such as cadmium, lead, nickel, zinc, mercury, copper, and the like. Additionally, methods for removal of heavy metals from various substances are disclosed, comprising separating selected heavy metals from selected substances by contacting the substances with an effective amount of the novel sulfur-containing chelate ligands for a sufficient time to form stable, irreversible ligand-metal precipitates, and removing such precipitates.

51 Claims, 6 Drawing Sheets

MULTIDENTATE SULFUR-CONTAINING LIGANDS

TECHNICAL FIELD

The present invention relates to binding, rendering insoluble, and precipitating a wide range of heavy metals, and more specifically to compounds and methods for multidentate binding or chelation of heavy metals utilizing a novel class of sulfur-containing ligands.

BACKGROUND OF THE INVENTION

Heavy metal pollution is an existing and growing worldwide problem. During the past few decades, federal and state governments have instituted environmental regulations to protect the quality of surface and ground water from heavy metals. In response to these regulatory requirements, numerous products have been developed to precipitate heavy metals from surface and ground water, and soil. An example of a reagent for precipitating divalent and univalent heavy metals from water is TMT-55, or 2,4,6-trimercaptotriazine, trisodium salt nonahydrate, manufactured by Degussa Corporation USA. The mode of action, chemistry, and stability of resulting heavy metal-trimercaptotriazine precipitates is unknown.

There are numerous industrial and environmental situations where ligands capable of binding metals are utilized for remediation purposes. For example, waste water issuing from waste treatment facilities, from the chlor-alkali industry, from the metal finishing industry, and from certain municipal landfills often presents a metal contamination problem. Similarly, the metal content of water exiting both functional and abandoned mines is a significant environmental issue in geographical areas with a heavy mining industry. Soils located in areas near natural gas pumphouses suffer a similar metal contamination problem. Thus, there is a need in the art for ligands capable of binding and precipitating heavy metals from both aqueous solutions and solid substrates such as soil.

It is known in the art to use sulfur-containing compounds to bind heavy metals. For example, Thio-Red® is a chemical reagent used for precipitating divalent heavy metals from water. This product is a complex aqueous solution of sodium (with or without potassium) thiocarbonate, sulfides, and other sulfur species. Thio-Red® ultimately removes Cu, Hg, Pb, and Zn from aqueous solutions through the formation of metal sulfides (i.e. CuS, HgS, PbS, and ZnS) rather than metal thiocarbonates. Sodium and potassium dialkyldithio-carbamates are also widely used as metal precipitants. However, the limited array of binding sites for heavy metals is a major concern with most ligands presently used on a commercial basis for heavy metal ion precipitation. Ligands that lack sufficient binding sites may produce metal precipitates that are unstable over time and under certain pH conditions. Such unstable precipitates may release bound metal back into the environment, thereby proving unsatisfactory as treatment or remediation agents. Further, these compounds may form simple metal sulfides which bacteria are capable of methylating (in the case of Hg, forming the water-soluble and highly toxic cation MeHg$^+$. Accordingly, there is a need in the art for chemical ligands which not only bind heavy metal ions, but also bind heavy metal ions in such a manner as to form stable, insoluble precipitates which remain stable over a range of environmental conditions and over extended periods of time.

SUMMARY OF THE INVENTION

In accordance with the purposes of the present invention as described herein, novel sulfur-containing chelate ligands are disclosed which bind heavy metals resulting in stable ligand-metal precipitates. The ligands of the present invention are suitable for binding any metal which is in or is capable of being placed in a positive oxidation state, including cadmium, iron, lead, nickel, zinc, mercury, copper, and the like. Additionally, methods for removal of heavy metals from various substances are disclosed, comprising separating selected heavy metals from selected substances by contacting said substances with an effective amount of said novel sulfur-containing chelate ligands for a sufficient time to form stable ligand-metal precipitates. The chelate ligands described herein may be used alone or in varying combinations to achieve the objects of the present invention. The ligand-metal precipitates formed by the ligands of the present invention are stable at a range of pH values from about 0 to about 14.

In one aspect, the present invention relates to chelate ligands consisting of a ring structure from which depend multiple alkyl chains terminating in sulfur-containing groups. The chelate ligands are of the general formula:

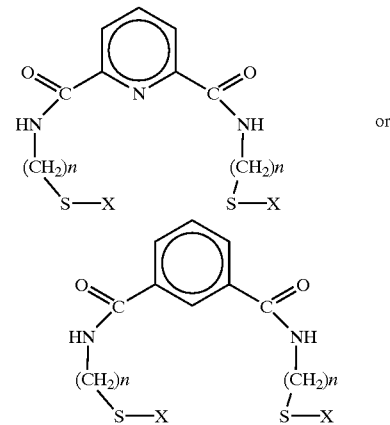

where n is an integer from 1–4, and X is any element selected from the elements contained in Group 1a of the Periodic Table of the Elements, i.e. H, Li, Na, K, Rb, Cs, or Fr. In one useful embodiment, the chelate ligands are of the formula:

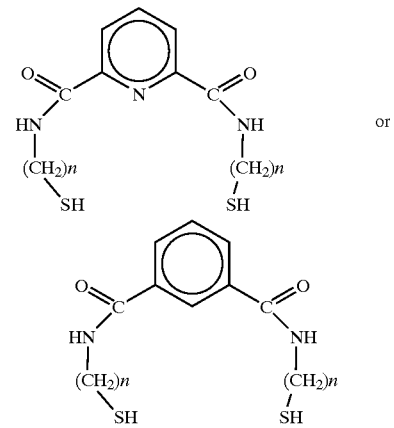

where n is an integer from 1–4. In another useful embodiment, the chelate ligands are of the formula:

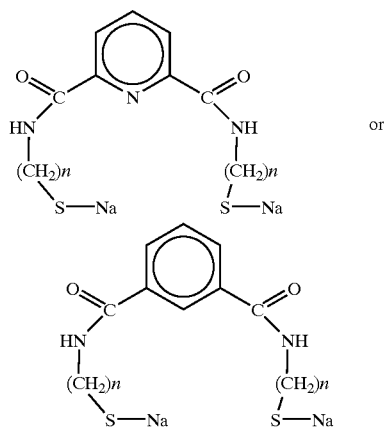

where n is an integer from 1–4.

The chelate ligand may be a pyridine-based ligand of the formula $C_{11}H_{15}N_3O_2S_2$, with pendant alkyl-thiol chains located at the 2,6 positions. In another particular embodiment, the chelate ligand may be a benzene-based compound of the formula $C_{12}H_{16}N_2O_2S_2$, with pendant alkyl-thiol chains located at the 1,3 positions. In yet other embodiments, the H group of the terminal thiol groups of the above benzene- and pyridine-based compounds may be replaced with a terminal Na to form the metallated product. While not wishing to be bound by any particular theory, it is believed that the stability of the metal complexes formed by use of the compounds of the present invention derive from multiple interactions between the metal and the sulfur and nitrogen atoms on the ligand, forming a multidentate bonding arrangement around a central metal atom.

In another aspect, the present invention relates to a method of removing metal ions from a starting material. The method of the present invention comprises contacting the starting material of choice with an effective amount of a novel sulfur-containing chelate ligand as described above for a sufficient time to form a stable ligand-metal complex precipitate, said metal remaining essentially irreversibly bound to said ligand at a range of pH values from about 0 to about 14.

In yet another aspect, the present invention relates to a method of treating water (e.g. surface, ground, or waste water) containing soft heavy metals, comprising admixing said water with an effective amount of the sulfur-containing chelate ligand as described above for a sufficient time to form a stable, irreversible ligand-metal complex precipitate, and separating said precipitate from said water.

In still another aspect, the present invention relates to a method of treating aqueous acid mine drainage or water from actual mining processes which contains soft heavy metals, comprising admixing said acid mine drainage or water from mining processes with an effective amount of the sulfur-containing chelate ligand as described above for a sufficient time to form a stable, irreversible ligand-metal complex precipitate, and separating said precipitate from said acid mine drainage.

In still another aspect, the present invention relates to a method of removing soft heavy metals from soils, comprising admixing said soils with an effective amount of the sulfur-containing chelate ligand as described above for a sufficient time to form a stable, irreversible ligand-metal complex precipitate. The soils so treated may be left in situ or removed for disposal without concerns regarding leaching of said metals into the environment.

Other objects of the present invention will become apparent to those skilled in this art from the following description wherein there is shown and described a preferred embodiment of this invention, simply by way of illustration of the modes currently best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification illustrates several aspects of the present invention and, together with the description, serves to explain the principles of the invention. In the drawing.

Figure 1A:
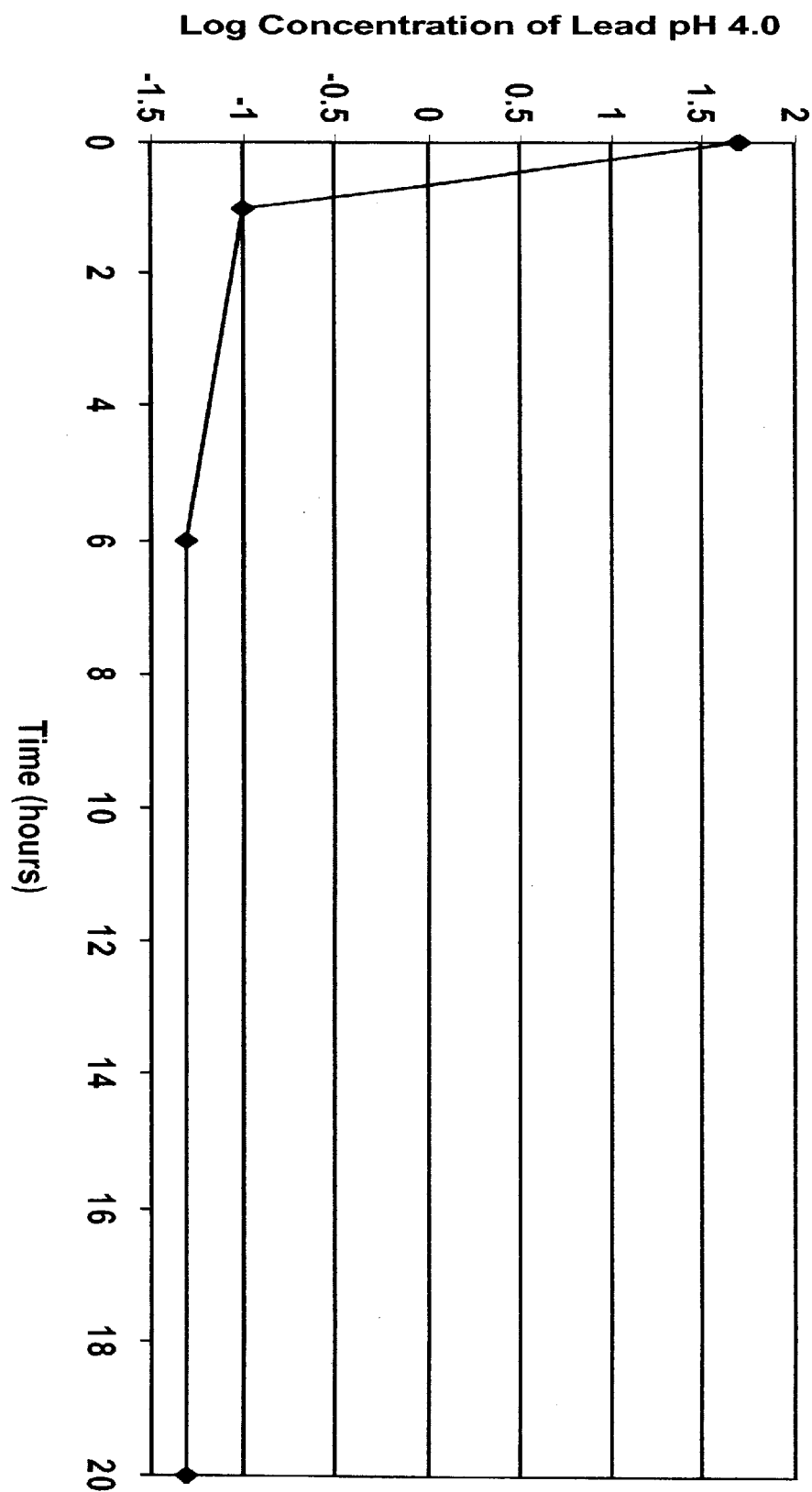
FIGS. 1a and 1b show binding and removal of lead from solution by the 1,3 benzene-thiol ligand of the present invention: (a) Removal of lead at pH 4.0 using a 1:1 molar ratio of ligand:metal; (b) Removal of lead at pH 6.0 using a 1:1 molar concentration of ligand:metal.

Reference will now be made in detail to the presently preferred embodiments of the invention, examples of which are illustrated in the accompanying drawing.

DETAILED DESCRIPTION OF THE INVENTION

As summarized above, the present invention relates to novel sulfur-containing chelate ligands which bind heavy metals, resulting in ligand-metal precipitates which remain stable at a wide range of pH values. The ligands of the present invention are suitable for binding metals which are in or are capable of being placed in a positive oxidation state, including cadmium, iron, lead, nickel, zinc, mercury, copper, and the like. In one aspect, the present invention relates to chelate ligands consisting of a ring structure from which depend multiple alkyl chains terminating in sulfur-containing groups. The chelate ligands are of the general formula:

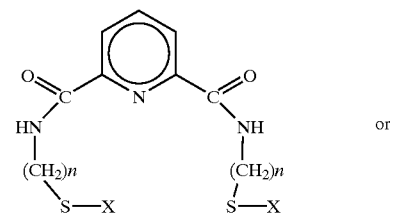

-continued

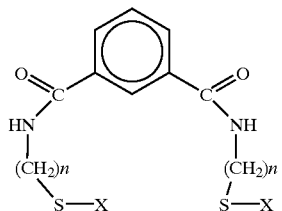

where n is an integer from 1–4, and X is any element selected from the group consisting of H, Li, Na, K, Rb, Cs, and Fr. In one useful embodiment, the chelate ligands are of the formula:

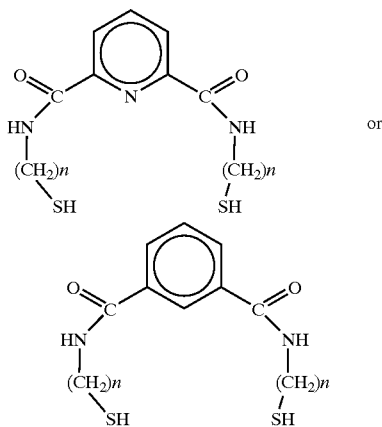

where n is an integer from 1–4.

In another useful embodiment, the chelate ligands are of the formula:

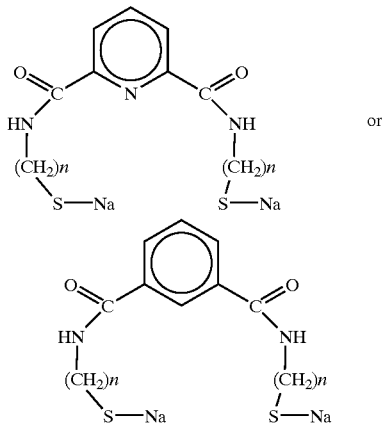

where n is an integer from 1–4.

The novel ligands of the present invention may be adapted to a variety of environmental situations requiring binding and/or removal of heavy metals, such as, e.g. treatment of industrial waste water, treatment of acid mine drainage, soil remediation, and the like. As will be appreciated by those skilled in the art, the chelate ligands of the present invention may be utilized alone or in varying combinations to achieve the objects of the present invention.

In another aspect, the present invention relates to a method of removing metal ions from a starting material. The method of the present invention comprises contacting the starting material of choice with an effective amount of a novel sulfur-containing chelate ligand as described above for a sufficient time to form a stable ligand-metal complex precipitate. Said ligand-metal complex precipitates remain stable at a range of pH values from about 0 to about 14.

In yet another aspect, the present invention relates to a method of treating water, such as surface, ground, or waste water, containing soft heavy metals, comprising admixing said water with an effective amount of the sulfur-containing chelate ligand as described above for a sufficient time to form a stable ligand-metal complex precipitate, and separating said precipitate from said water.

In still another aspect, the present invention relates to a method of treating aqueous acid mine drainage or water from actual mining processes containing soft heavy metals, comprising admixing said acid mine drainage or water from actual mining processes with an effective amount of the sulfur-containing chelate ligand as described above for a sufficient time to form a stable ligand-metal complex precipitate, and separating said precipitate from said acid mine drainage.

In still another aspect, the present invention relates to a method of remediation of soils containing soft heavy metals, comprising admixing said soils with an effective amount of the sulfur-containing chelate ligand as described above for a sufficient time to form a stable ligand-metal complex precipitate. The soils so treated may then be left in situ or removed for disposal without concerns regarding leaching of said metals into the environment.

The compositions and methods of the present invention may be accomplished by various means which are illustrated in the examples below. These examples are intended to be illustrative only, as numerous modifications and variations will be apparent to those skilled in the art.

EXAMPLE 1

In this example, 3.14 grams of 2-aminoethanethiol hydrochloride was dissolved in chloroform, and 3.88 ml of triethylamine were added. 2.81 grams of isophthaloyl chloride was then dissolved in chloroform under nitrogen. 2-aminoethanethiol hydrochloride and 1,3-isophthaloyl chloride, prepared as described supra, were then slowly mixed, and the resulting solution was stirred under nitrogen in an ice bath for several hours. The resulting solution was then filtered under nitrogen, and several water/chloroform extractions performed. Following removal of excess solvent by rotary evaporation or distillation, the resulting product was passed through a silica gel column using ethyl acetate/chloroform. Excess solvent was removed by rotary evaporation and vacuum-drying, resulting in a white precipitate. The resulting 1,3 benzene-thiol product had the formula:

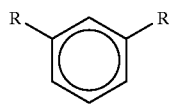

where R is an alkyl thio chain containing two methyl groups.

EXAMPLE 2

In this example, 2.76 grams of aminomethanethiol hydrochloride are dissolved in chloroform, and 7.72 ml of triethylamine are added. 2.81 grams of isophthaloyl chloride are then dissolved in chloroform under nitrogen. Aminomethanethiol hydrochloride and isophthaloyl chloride, prepared as described supra, are then slowly mixed, and the resulting solution is stirred under nitrogen in an ice bath for several hours. The resulting solution is then filtered under nitrogen, and several water/chloroform extractions are performed. Excess solvent is removed by rotary evaporation or distillation, and the resulting product is passed through a silica gel column using ethyl acetate/chloroform. Excess solvent is removed by rotary evaporation and vacuum-drying, resulting in a white precipitate. The resulting 1,3 benzene-thiol product has the formula:

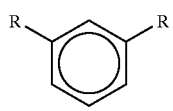

where R is an alkyl thiol chain containing one methyl group.

EXAMPLE 3

This example, 3.53 grams of 3-aminopropanethiol hydrochloride are dissolved in chloroform, and 7.72 ml of triethylamine are added. 2.81 grams of isophthaloyl chloride are then dissolved in chloroform under nitrogen. 3-aminopropanethiol hydrochloride and isophthaloyl chloride, prepared as described supra, are then slowly mixed, and the resulting solution is stirred under nitrogen in an ice bath for several hours. The resulting solution is then filtered under nitrogen, and several water/chloroform extractions are performed. Excess solvent is removed by rotary evaporation or distillation, and the resulting product is passed through a silica gel column using ethyl acetate/chloroform. Excess solvent is removed by rotary evaporation and vacuum-drying, resulting in a white precipitate. The resulting 1,3 benzene-thiol product has the formula:

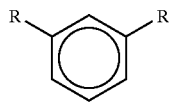

where R is an alkyl thiol chain containing three methyl groups.

EXAMPLE 4

In this example, 3.92 grams of 4-aminobutanethiol hydrochloride are dissolved in chloroform, and 7.72 ml of triethylamine are added. 2.81 grams of isophthaloyl chloride are then dissolved in chloroform under nitrogen. 4-aminobutanethiol hydrochloride and isophthaloyl chloride, prepared as described supra, are then slowly mixed, and the resulting solution is stirred under nitrogen in an ice bath for several hours. The resulting solution is then filtered under nitrogen, and several water/chloroform extractions are performed. Excess solvent is removed by rotary evaporation or distillation, and the resulting product is passed through a silica gel column using ethyl acetate/chloroform. Excess solvent is removed by rotary evaporation and vacuum-drying, resulting in a white precipitate. The resulting 1,3 benzene-thiol product has the formula:

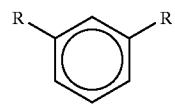

where R is an alkyl thiol chain containing four methyl groups.

EXAMPLE 5

In this example, 5 grams of 2,6 pyridine dicarbonyl dichloride were dissolved in chloroform under nitrogen. 5.56 grams of 2-aminothioethane thiol hydrochloride were also dissolved in chloroform under nitrogen, and slowly added to the acid chloride solution in an ice bath. Approximately 13.66 ml of triethylamine were added. The resulting mixture was stirred under nitrogen for 2–4 hours. The resulting yellow/brown solution was filtered under nitrogen, extracted three times with water/chloroform, refiltered under nitrogen, and excess solvent was removed by rotary evaporation or distillation. The resulting product was redissolved in chloroform and passed through a silica gel column using 70% ethyl acetate/30% chloroform. The resulting white precipitate was a 2,6 pyridine thiol product with the formula:

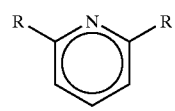

where R is an alkyl thiol chain containing two methyl groups.

EXAMPLE 6

In this example, 432 grams (1.5 mol) of a 1,3 benzene thiol ligand prepared as described in Example 1 was dissolved in 150 ml of ethanol. An excess of sodium hydroxide solution of not less than 3 mol but not more than 12 mol was added and stirred for at least 2 hours. The resulting product was crystallized, and excess ethanol removed under vacuum. The resulting 1,3 benzene metallate product had the formula:

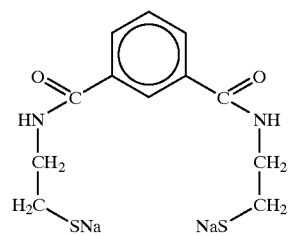

EXAMPLE 7

This example, the 1,3 benzene thiol ligand (100 g), prepared as described in Example 1, is dissolved in 100 ml of $CHCl_3$ Next, HCl is slowly bubbled through the above solution over a period of several hours. Excess solution is removed by rotary evaporation or distillation, resulting in a white precipitate which is the ammonium chloride salt of the ligand.

EXAMPLE 8

Figure 1B:
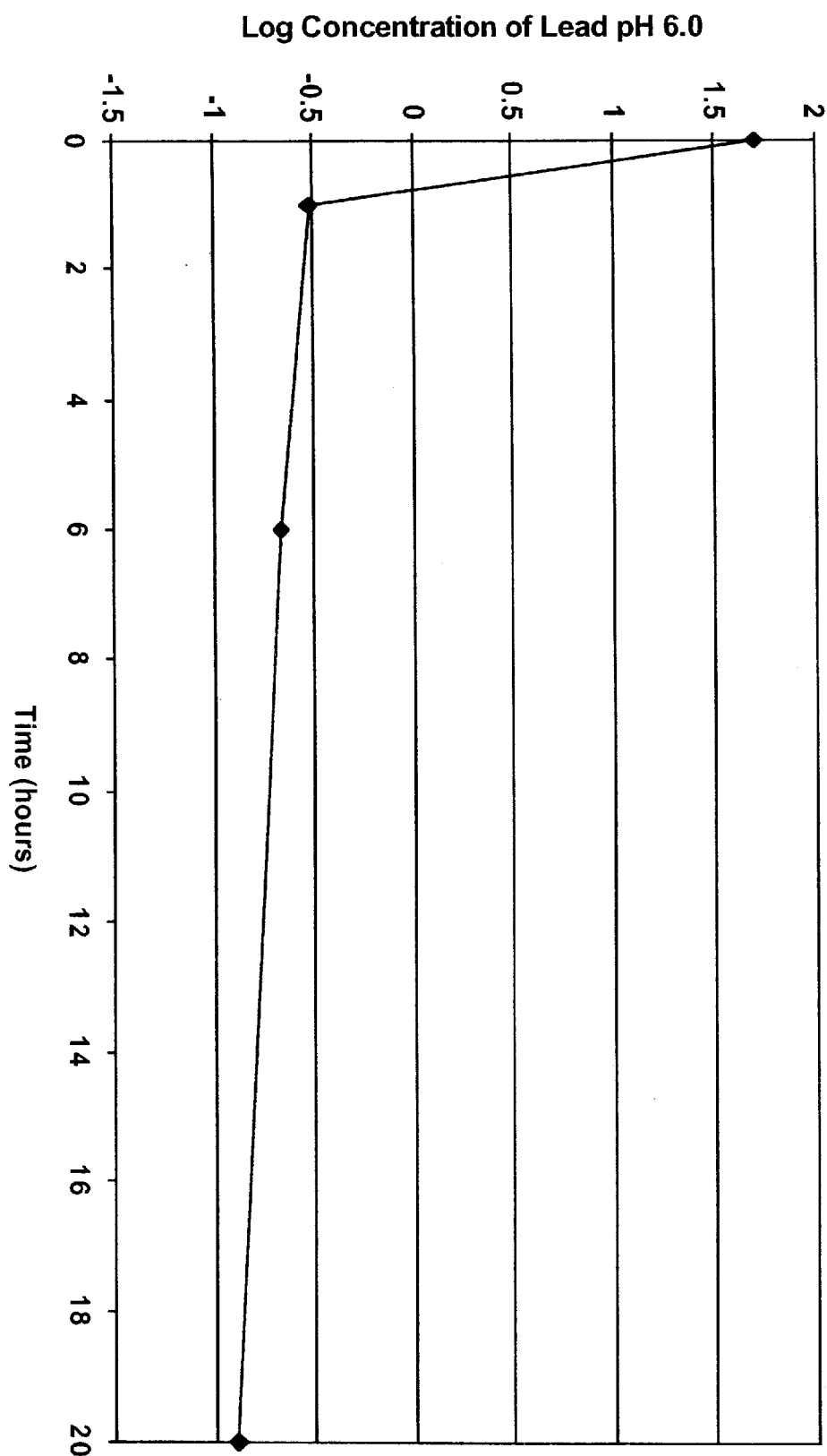
Figure 2A:
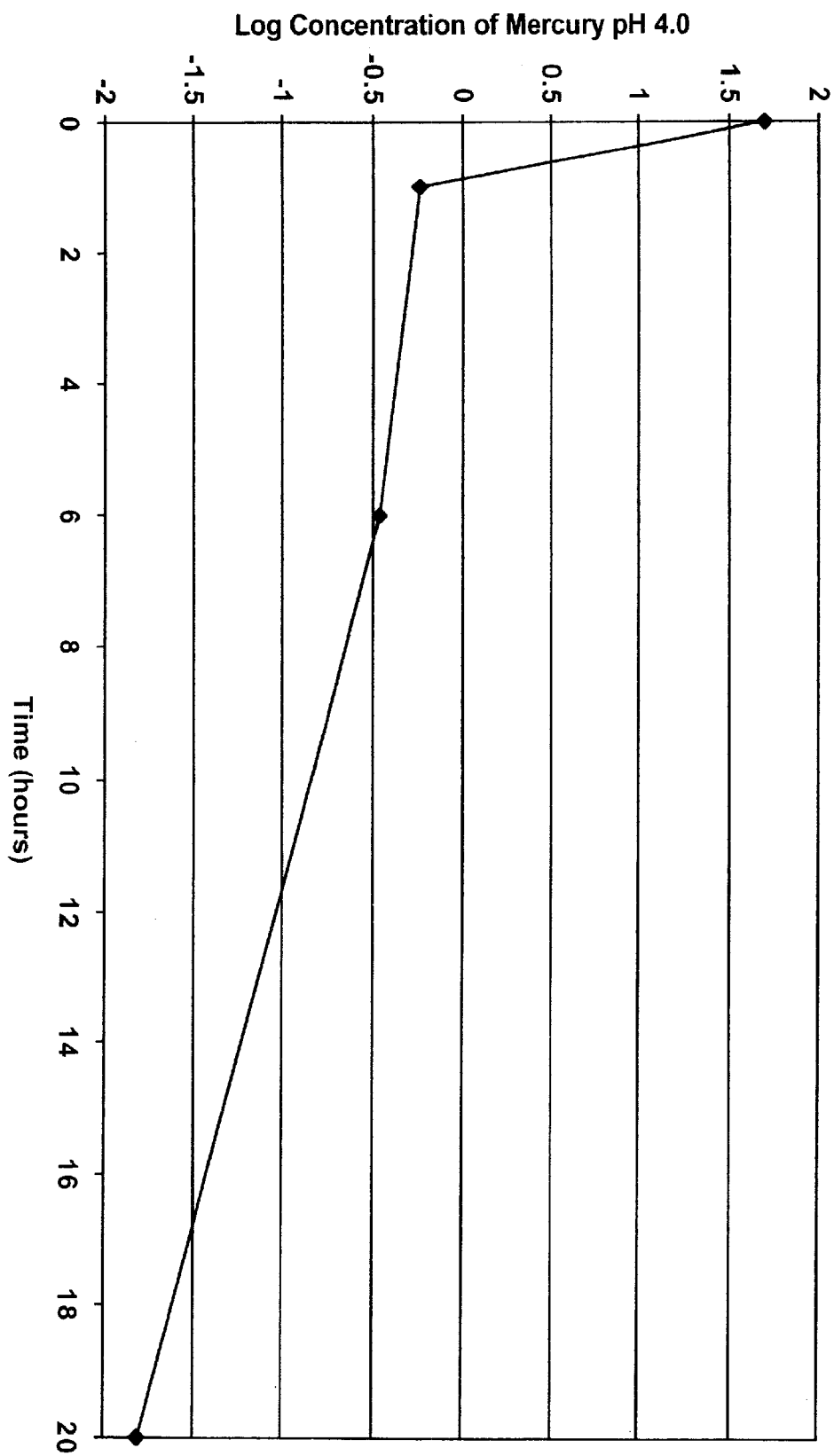
FIGS. 2a and 2b show binding and removal of mercury from solution of pH 4.0 by the 1,3 benzene-thiol ligand of the present invention: (a) Removal of mercury using a 1:1 molar ratio of ligand:metal; (b) Removal of mercury using 10% in excess of a 1:1 molar ration of ligand:metal.
Figure 2B:
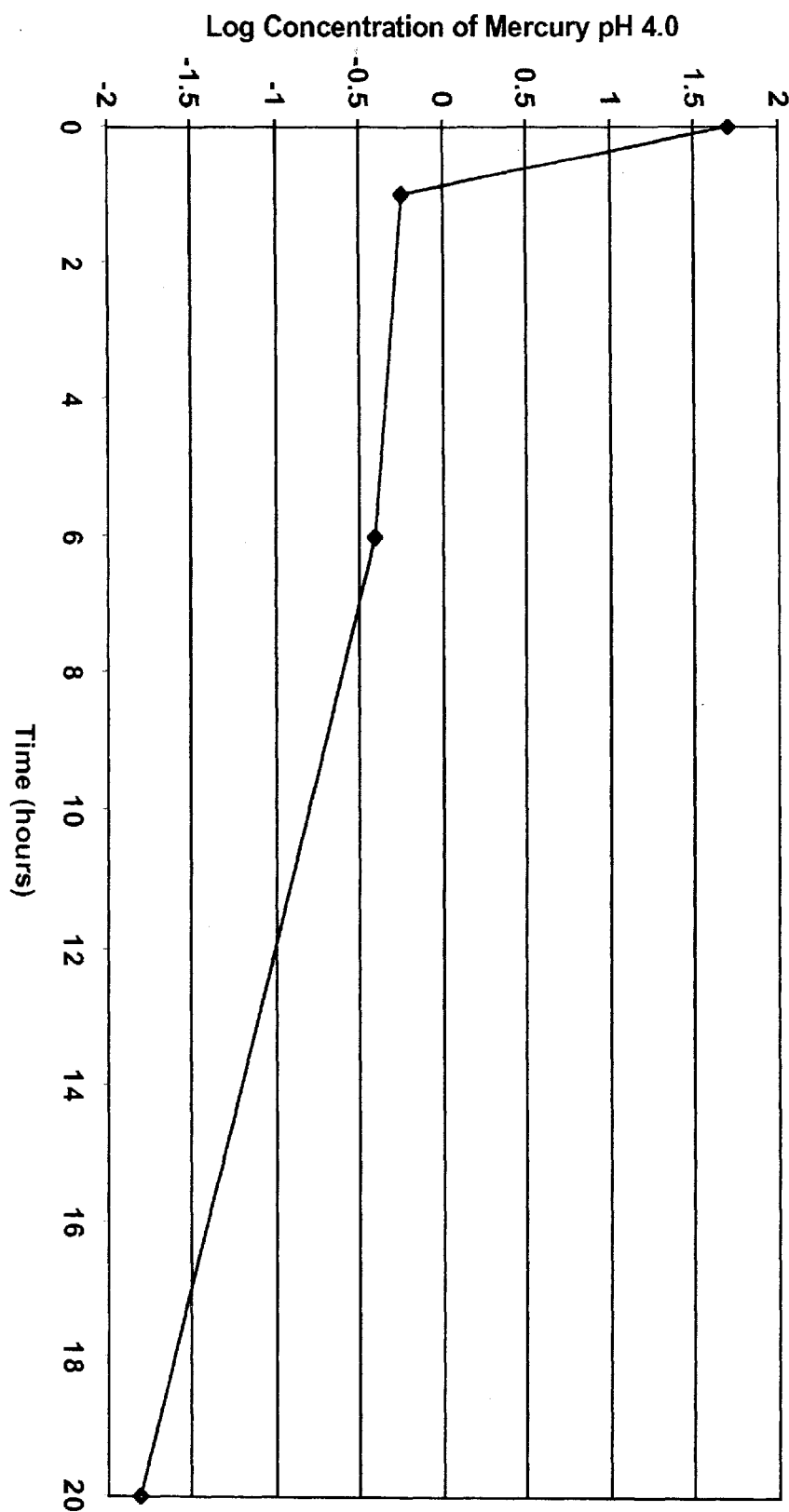
Figure 3A:
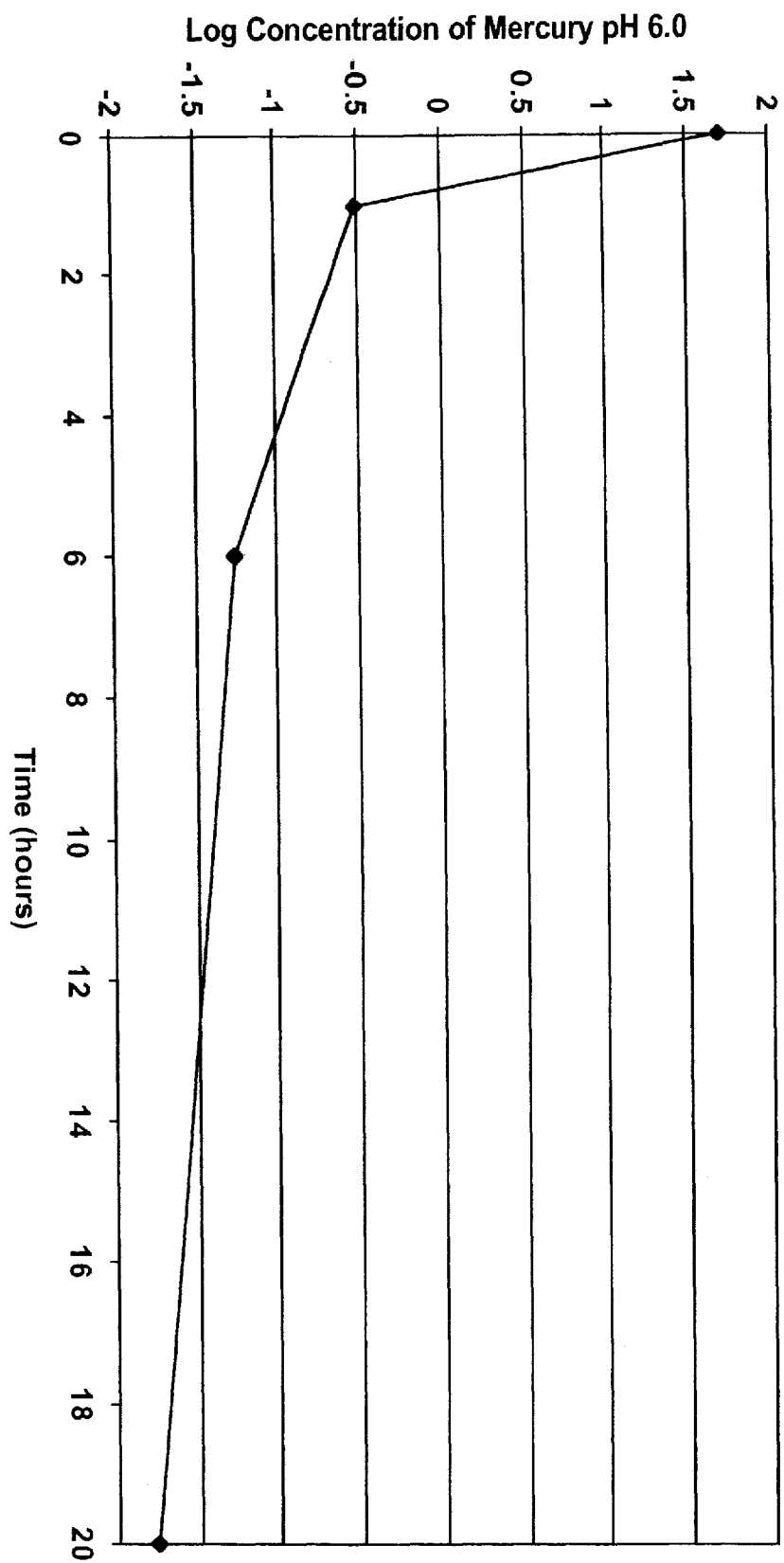
FIGS. 3a and 3b show binding and removal of mercury from solution at pH 6.0 by the 1,3 benzene-thiol ligand of the present invention: (a) Removal of mercury using a 1:1 molar ratio ligand: metal; (b) Removal of mercury using 10% in excess of a 1:1 molar ration of ligand:metal.
Figure 3B:
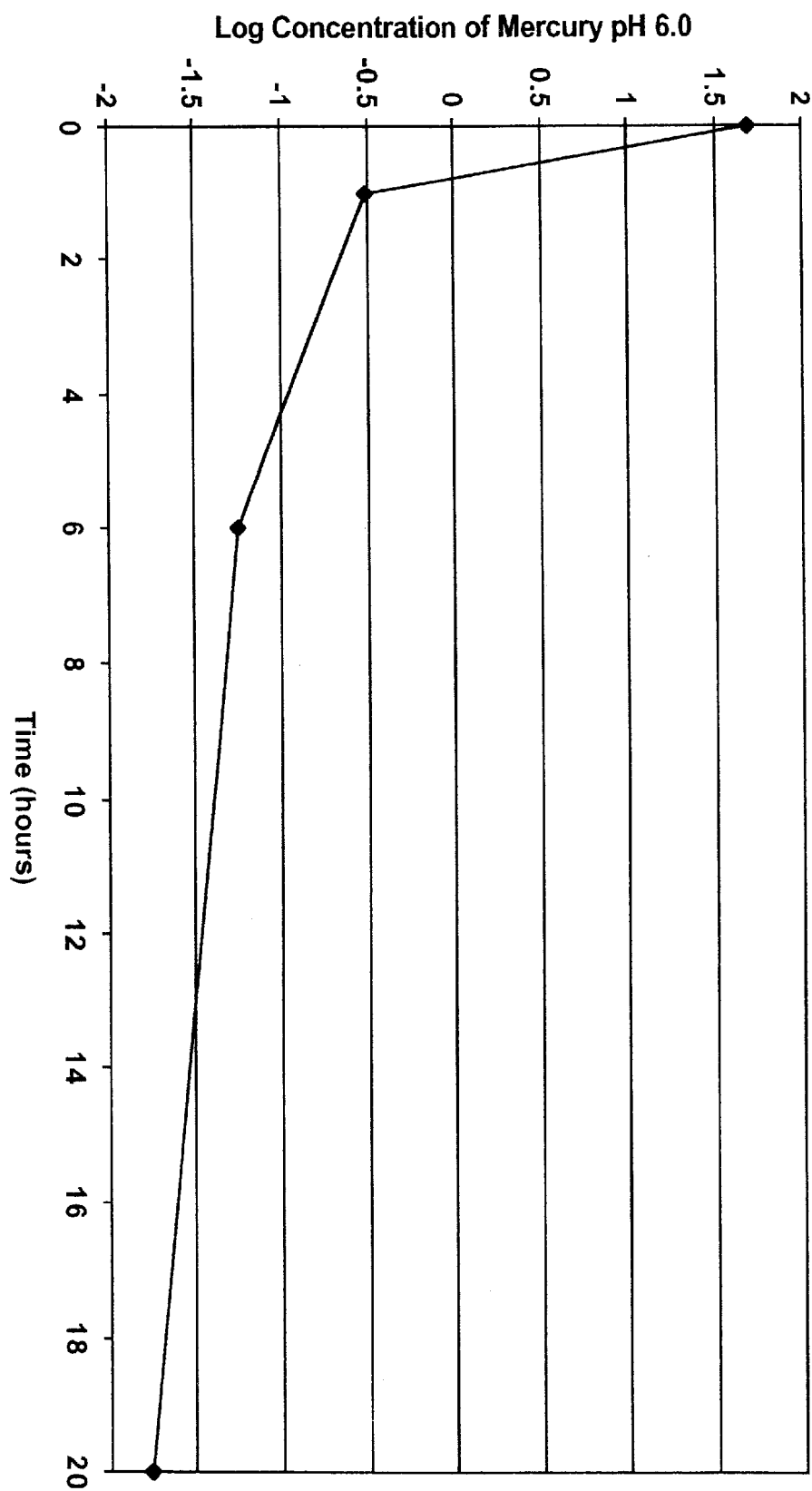

Lead (50 ppm in 40% ethanol/60% water) samples and a 1,3 benzene thiol ligand prepared as described in Example 1 were admixed in a 1:1 molar ratio, resulting in a solution of pH 4.0. The experiment was repeated with addition of an acetic acid/sodium acetate buffer to maintain a pH of 6.0. Aliquots of the solutions were collected at 1, 6, and 20 hours, filtered (0.2 μm filters), and analyzed for removal of lead by inductively-coupled plasma spectrometry (1999 Duo HR Iris Advanced Inductive Coupled Plasma Spectrometer). As illustrated in FIG. 1A, maximum lead removal was observed at 6 hours at pH 4.0 (99.9% of lead removed). Maximum lead removal was observed at 20 hours at pH 6.0 (99.7% of lead removed; FIG. 1B). However, it should be noted that, regardless of pH, the concentration of lead in solution was below the Environmental Protection Agency limit of 5 ppm within 1 hour.

EXAMPLE 9

Mercury (50 ppm in 40% ethanol/60% water) and a 1,3 benzene thiol ligand prepared as described in Example 1 were admixed with ligand added at 10% excess of a 1:1 molar ratio. The experiment was repeated with addition of acetic acid/sodium acetate buffer to maintain pH of the solution at 6.0. Samples of the solution were collected at 1, 6, and 20 hours, filtered (0.2 μm filters) and analyzed for removal of mercury by an EPA cold vapor technique (Method 7470, US Environmental Protection Agency, 1986, "Test Methods for Evaluating Solid Wastes: Volume 1A: Laboratory Manual: Physical/Chemical Methods," SW-846, 3d Ed., Office of Solid Waste and Emergency Response, Washington, D.C., incorporated herein by reference). As can be seen in FIGS. 2A, 2B, 3A, and 3B, regardless of pH a maximum removal of 99.7% of mercury from solution was achieved by 20 hours.

EXAMPLE 10

Cadmium (50 ppm in 39% ethanol/61% water) and a 2,6 pyridine thiol ligand prepared as described in Example 2 were admixed in a 1:1 molar ratio, producing a solution with pH 4.5. The experiment was repeated with addition of an acetic acid/sodium acetate buffer to maintain pH at 6.0. Additionally, the experiment was repeated with an 8% increase (above the 1:1 molar ratio) in the amount of pyridine thiol ligand added. Aliquots were removed at 4 and 24 hours, filtered (0.2 μm filters) and analyzed for removal of cadmium by standard flame atomic absorption spectrometry (Perkin-Elmer flame Atomic Absorption Spectrometer, Model 3100). As can be seen in Table 1, at pH 4.5, maximum cadmium removal (47.14%) was seen at 18 hours for the 1:1 molar ratio of cadmium/pyridine thio ligand. At pH 6.0, 99.7% cadmium was removed from solution for the 8% higher ligand concentration.

TABLE 1

$Cd^{+2}$ binding by Pyridine-Thiol Ligand.

| Time Sample Removed | Amount of Excess Pyridine-Thiol Ligand | Initial Concentration (ppm) | Final Concentration (ppm) | Cadmium Removed (ppm) | Percentage of Cadmium Removed | pH |
|---|---|---|---|---|---|---|
| 4 hours | none | 227.84 | 68.57 | 159.27 | 69.90% | 4.0 |
| 24 hours | none | 227.84 | 71.71 | 156.13 | 68.53% | 4.0 |
| 2 hours | none | 50.00 | 26.99 | 23.01 | 46.02% | 4.5 |
| 4 hours | none | 50.00 | 26.86 | 23.14 | 46.28% | 4.5 |
| 18 hours | none | 50.00 | 26.43 | 23.57 | 47.14% | 4.5 |
| 1 hour | none | 50.00 | 4.40 | 45.60 | 92.20% | 6.0** |
| 16 hours | none | 50.00 | 4.16 | 45.84 | 91.68% | 6.0** |
| 1 hour | *8.00% | 50.00 | 0.15 | 49.85 | 99.70% | 6.0** |
| 12 hours | *8.00% | 50.00 | 0.06 | 49.94 | 99.88% | 6.0** |

Except where noted, all reactions carried out at a 1:1 molar ratio of pyridine-thiol ligand:metal.
*8% dose increase
**pH controlled with buffer

EXAMPLE 11

Copper (50 ppm in 39% ethanol/61% water) and a 2,6 pyridine thiol ligand prepared as described in Example 2 were admixed in a 1:1 molar ratio. The experiment was repeated with addition of an acetic acid/sodium acetate buffer to maintain pH at 6.0. Additionally, the experiment was repeated with an 8% increase (above a 1:1 molar ratio) in the amount of pyridine thiol ligand added. Aliquots were removed at 1 and 4 hours, filtered (0.2 μm filters) and analyzed for removal of copper by standard flame atomic absorption spectrometry as in Example 10. Maximum copper removal (99.56%) occurred at 1 hour for the 8% increased pyridine thiol ligand dose at pH 4.5 (Table 2). No significant increases in copper removal were noted for the buffered solution, nor beyond 4 hours.

TABLE 2

$Cu^{+2}$ binding by Pyridine-Thiol Ligand.

| Time Sample Removed | Amount of Excess Pyridine-Thiol Ligand | Initial Concentration (ppm) | Final Concentration (ppm) | Copper Removed (ppm) | Percentage of Copper Removed | pH |
|---|---|---|---|---|---|---|
| 1 hour | none | 50.00 | 12.28 | 37.72 | 75.44% | 4.5 |
| 1 hour | *8.00% | 50.00 | <.11 | 45.87 | 91.74% | 4.5 |
| 4 hours | none | 50.00 | 4.13 | 45.87 | 91.74% | 4.5 |
| 4 hours | *8.00% | 50.00 | 0.92 | 49.08 | 98.16% | 4.5 |
| 1 hour | none | 50.00 | 1.05 | 48.95 | 97.80% | 6.0** |
| 1 hour | *8.00% | 50.00 | 1.35 | 48.66 | 97.32% | 6.0** |
| 4 hours | none | 50.00 | 1.56 | 48.44 | 96.88% | 6.0** |

Except where noted, all reactions carried out at a 1:1 molar ratio of pyridine-thiol ligand:metal.
*8% dose increase
**pH controlled with buffer

EXAMPLE 12

Samples of mercury, lead, cadmium, copper, and iron(II) were prepared essentially as described in Examples 8–11, and the ability of the 1,3 benzene thiol and 2,6 pyridine thiol ligands, synthesized as described in Examples 1 and 2 respectively, to remove said metals from solution was evaluated. Metal binding was tested at pH values of 4.0 and 6.0. The ligands of the present invention removed over 98% of all metals tested, with the sole exception of Cu at pH 6.0 (Table 3). However, almost 94% of Cu was removed. Additionally, in all cases where published EPA limits for particular metals are available, the ligands of the present invention reduced the concentration of metals in solution to below EPA limits.

TABLE 3

Removal of metals from aqueous solution

| Ligand | Metal | pH | Initial Conc. (ppm) | Final Conc. (ppm) | % Removal | EPA Limits (ppm) |
|---|---|---|---|---|---|---|
| 1,3 benzene thiol | Hg | 4.0 | 50.0000 | 0.0155 | 99.97 | 0.2 |
| 1,3 benzene thiol | Hg | 6.0 | 50.0000 | 0.0174 | 99.97 | 0.2 |
| 1,3 benzene thiol | Pb | 4.0 | 50.0000 | 0.05 | 99.90 | 5.0 |
| 1,3 benzene thiol | Pb | 6.0 | 50.0000 | 0.13 | 99.74 | 5.0 |
| 1,3 benzene thiol | Cd | 4.0 | 50.0000 | 0.92 | 98.16 | 1.0 |
| 1,3 benzene thiol | Cd | 6.0 | 50.0000 | 0.11 | 99.78 | 1.00 |
| 1,3 benzene thiol | Cu | 4.0 | 50.0000 | 0.27 | 99.46 | |
| 1,3 benzene thiol | Cu | 6.0 | 50.0000 | 3.02 | 93.96 | |
| 1,3 benzene thiol | Fe(II) | 4.0 | 50.0000 | 0.8961 | 98.21 | |
| 1,3 benzene thiol | Fe(II) | 6.0 | 50.0000 | 0.0092 | 99.98 | |
| 2,6 pyridine thiol | Hg | 4.0 | 50.0000 | 0.1321 | 99.74 | 0.2 |
| 2,6 pyridine thiol | Hg | 6.0 | 50.0000 | 0.0984 | 99.80 | 0.2 |
| 2,6 pyridine thiol | Pb | 4.0 | 50.0000 | 0.07 | 99.86 | 5.0 |
| 2,6 pyridine thiol | Pb | 6.0 | 50.0000 | 0.80 | 98.39 | 5.0 |
| 2,6 pyridine thiol | Cd | 4.0 | 50.0000 | 0.94 | 98.12 | 1.00 |
| 2,6 pyridine thiol | Cd | 6.0 | 50.0000 | 0.06 | 99.88 | 1.00 |
| 2,6 pyridine thiol | Cu | 4.0 | 50.0000 | <0.0093 | >99.98 | |
| 2,6 pyridine thiol | Cu | 6.0 | 50.0000 | <0.0093 | >99.98 | |

EXAMPLE 13

The ability of a 1,3 benzene thiol ligand to retain bound mercury over time and at various pH ranges was tested. The 1,3 benzene thiol ligand synthesized as described in Example 1 was allowed to bind Hg at a 1:1 molar ratio. Acetic acid/sodium acetate buffer was used to maintain pH of samples at 4.0, 6.0, or 10.0. Samples were tested for Hg leaching by an EPA cold vapor technique as described in Example 9 at 2, 30, and 60 days. Regardless of pH or time of incubation, less than 0.013% of bound Hg was released by the 1,3 benzene thiol ligand of the present invention (Table 4), demonstrating the stability of the metal-ligand complexes formed by the ligands.

TABLE 4

Leaching of 1,3 benzene thiol-Mercury in solution.

| Complex | pH | Time (days) | Initial Conc. Of Hg (ppm)* | Leached Conc. Of Hg (ppm) | % Hg Leached |
|---|---|---|---|---|---|
| 1,3 benzene thiol - Hg | 4 | 2 | 3990 | <0.5 | <0.013 |
| 1,3 benzene thiol - Hg | 6 | 2 | 3990 | <0.5 | <0.013 |
| 1,3 benzene thiol - Hg | 10 | 2 | 3990 | <0.5 | <0.013 |
| 1,3 benzene thiol - Hg | 4 | 30 | 3990 | <0.5 | <0.013 |
| 1,3 benzene thiol - Hg | 6 | 30 | 3990 | <0.5 | <0.013 |
| 1,3 benzene thiol - Hg | 10 | 30 | 3990 | <0.5 | <0.013 |
| 1,3 benzene thiol - Hg | 4 | 60 | 3990 | <0.5 | <0.013 |

TABLE 4-continued

Leaching of 1,3 benzene thiol-Mercury in solution.

| Complex | pH | Time (days) | Initial Conc. Of Hg (ppm)* | Leached Conc. Of Hg (ppm) | % Hg Leached |
|---|---|---|---|---|---|
| 1,3 benzene thiol - Hg | 6 | 60 | 3990 | <0.5 | <0.013 |
| 1,3 benzene thiol - Hg | 10 | 60 | 3990 | <0.5 | <0.013 |

*NOTE:
The initial concentration of Hg) is based on the original amount of Hg-Ligand complex tested and assumes 100% leached.

EXAMPLE 14

Ability of a 1,3 benzene thiol ligand to retain bound iron over time and at various pH ranges was tested. The 1,3 benzene thiol ligand synthesized as described in Example 1 was allowed to bind Fe(II) at a 1:1 molar ratio. Acetic acid/sodium acetate buffer was used to maintain pH of samples at 0.0 or 4.0. Samples were tested for Fe(II) leaching by standard inductively coupled plasma spectrometry as described in Example 8 at 1, 7, and 30 days. Regardless of pH or time of incubation, the 1,3 benzene thiol ligand of the present invention retained at least 94% of bound Fe(II) over the experimental period (Table 5). The metal complexes formed by the ligands of the present invention are therefore shown to be stable over time.

TABLE 5

Leaching of 1,3 benzene thiol - iron (II) in solution.

| Complex | pH | Time (days) | Initial Fe(II) Conc. (ppm)* | Conc. Of Fe(II) Leached (ppm) | % Fe Leached |
|---|---|---|---|---|---|
| 1,3-benzene thiol - Fe(II) | 0 | 1 | 1650.00 | 94.10 | 5.90 |
| 1,3-benzene thiol - Fe(II) | 4 | 1 | 1650.00 | 98.21 | 1.79 |
| 1,3-benzene thiol - Fe(II) | 0 | 7 | 1650.00 | 94.70 | 5.30 |
| 1,3-benzene thiol - Fe(II) | 4 | 7 | 1650.00 |  | 2.29 |
| 1,3-benzene thiol - Fe(II) | 0 | 30 | 1650.00 | 94.79 | 5.21 |
| 1,3-benzene thiol - Fe(II) | 4 | 30 | 1650.00 | 94.15 | 5.85 |

*The initial concentration of Fe(II) is based on the original amount of Fe(II)-Ligand complex tested and assumes 100% leached.

EXAMPLE 15

Ability of the 1,3 benzene thiol ligand of the present invention to retain bound iron over time and at various pH ranges in either deionized water or hydrogen peroxide solution was tested. The 1,3 benzene thiol ligand synthesized as described in Example 1 was allowed to bind Fe(II) at a 1:1 molar ratio. Acetic acid/sodium acetate buffer was used to maintain pH of samples at 0.0 or 4.0 in either deionized water or a 1.0% solution of hydrogen peroxide in deionized water. Samples were tested for Fe(II) leaching by standard inductively coupled plasma spectrometry as discussed in Example 8 at 1, 7, and 30 days. The 1,3-benzene thiol ligand retained Fe(II) best at pH 4.0 in deionized water (>97% retention; Table 6). However, in no case did Fe(II) retention fall below 86%, even after 30 days of incubation. The metal complexes formed by the ligands of the present invention are therefore shown to remain stable even at varying pH ranges, and in the presence of potentially interfering ions.

TABLE 6

Average Results of 1,3 benzene thiol-iron (II) leaching in solution.

| Sample | Time (days) | Mass (grams) of Ligand Fe(II) Complex | Mass (grams) of Fe(II) | Leached Mass (grams) of Fe(II) | % Iron Leached | % Iron Unaffected |
|---|---|---|---|---|---|---|
| A | 1 | 1.000 | 0.165 | 0.011 | 6.64 | 93.36 |
| B | 1 | 1.000 | 0.165 | 0.010 | 5.90 | 94.10 |
| C | 1 | 1.000 | 0.165 | 0.011 | 6.64 | 93.36 |
| D | 1 | 1.000 | 0.165 | 0.003 | 1.79 | 98.21 |
| A | 7 | 1.000 | 0.165 | 0.021 | 13.00 | 87.00 |
| B | 7 | 1.000 | 0.165 | 0.017 | 10.12 | 89.88 |
| C | 7 | 1.000 | 0.165 | 0.021 | 12.86 | 87.14 |
| D | 7 | 1.000 | 0.165 | 0.004 | 2.29 | 97.71 |
| A | 30 | 1.000 | 0.165 | 0.022 | 13.05 | 86.95 |
| B | 30 | 1.000 | 0.165 | 0.017 | 10.22 | 89.78 |
| C | 30 | 1.000 | 0.165 | 0.021 | 13.02 | 86.98 |
| D | 30 | 1.000 | 0.165 | 0.004 | 2.53 | 97.47 |

Sample A: pH 0.0 in 1.0% Hydrogen Peroxide
Sample B: pH 0.0 in Deionized Water
Sample C: pH 4.0 in 1.0% Hydrogen Peroxide Solution.
Sample D: pH 4.0 in deionized Water
Metal content analyzed by inductively-coupled plasma spectrometry.

EXAMPLE 16

Samples of acid mine drainage were collected at various stages post-discharge. Samples were collected at the borehole, at two areas of the discharge pipe (3 and 4 inch diameter), at the point discharge site, and downstream of the point discharge site. Collected samples were analyzed for a range of metals by inductively coupled plasma spectrometry before (Table 7) and after (Tables 8–10) treatment with a 1,3 benzene metallate ligand prepared as described in Example 6. Samples were tested at 1, 6, and 20 hours after addition of an excess of the 1,3 benzene metallate ligand. The ligand bound all metals evaluated which were present at detectable concentrations in acid mine drainage. The ligand was particularly effective in binding Cd, Cu, Fe, Mg, and Mn (Tables 7 and 8). For example, Fe was detected in acid mine drainage at a concentration of 194.2 ppm at the borehole, and 2.703 ppm downstream of the discharge point (Table 7).

TABLE 7

Metal content of acid mine drainage before treatment with disodium benzenethio ligand (BDETNa$_2$).

| Element | Borehole Conc. (ppm) | 3" Pipe Conc. (ppm) | 4" Pipe Conc. (ppm) | Discharge Conc. (ppm) | Downstream Conc. (ppm) |
|---|---|---|---|---|---|
| Al | 0.483 | 0.515 | 0.452 | 0.641 | 0.567 |
| Sb | 1.306 | 0.394 | 0.339 | 0.249 | 0.210 |
| As | 0.0169 | <0.0118 | <0.0118 | <0.0118 | <0.0118 |
| Ba | 0.007 | 0.015 | 0.019 | 0.012 | 0.018 |
| Be | 0.0012 | 0.0010 | <0.0002 | <0.0002 | <0.0002 |
| Cd | 0.0104 | <0.0075 | <0.0075 | <0.0075 | <0.0075 |
| Cr | <0.0142 | <0.0142 | <0.0142 | <0.0142 | <0.0142 |
| Co | 0.023 | 0.011 | 0.010 | 0.008 | 0.007 |
| Cu | 0.0118 | <0.0093 | <0.0093 | <0.0093 | <0.0093 |
| Fe | 194.200 | 28.370 | 24.225 | 2.876 | 2.703 |
| Pb | <0.02 | <0.02 | <0.02 | <0.02 | <0.02 |
| Mg | 57.430 | 57.105 | 49.390 | 52.640 | 42.885 |
| Mn | 4.645 | 2.652 | 2.182 | 1.254 | 0.913 |
| Ni | 0.037 | 0.013 | 0.012 | 0.011 | 0.016 |
| Se | 0.0215 | 0.0220 | 0.0290 | <0.0112 | <0.0112 |
| Ag | 0.0322 | <0.0102 | <0.0102 | <0.0102 | <0.0102 |
| Sr | 3.526 | 5.676 | 4.920 | 5.104 | 4.294 |
| Tl | <0.0748 | <0.0748 | <0.0748 | <0.0748 | <0.0748 |
| Sn | <0.1382 | <0.1382 | <0.1382 | <0.1382 | <0.1382 |
| V | 0.848 | 0.290 | <0.0134 | <0.0134 | <0.0134 |

One hour after treatment of the acid mine drainage with ligand, the concentration of Fe was 0.8961 ppm at the borehole and was below detectable levels at any sampling point thereafter (Table 8). Iron concentration of the borehole sample was reduced to 0.0092 ppm after 6 hours of treatment with ligand (Table 9), and was below detectable limits by 20 hours of treatment (Table 10).

TABLE 8

Metal content of acid mine drainage after treatment for one hour with BDETNa$_2$.

| Element | Borehole Conc. 1 hr. (ppm) | 3" Pipe Conc. 1 hr. (ppm) | 4" Pipe Conc. 1 hr. (ppm) | Discharge Conc. 1 hr. (ppm) | Downstream conc. 1 hr. (ppm) |
|---|---|---|---|---|---|
| Al | 0.311 | 0.215 | 0.116 | <0.0409 | 0.141 |
| Sb | 0.240 | 0.136 | 0.138 | 0.152 | 0.136 |
| As | <0.0118 | <0.0118 | <0.0118 | <0.0118 | <0.0118 |
| Ba | 0.006 | 0.014 | 0.004 | <.0031 | 0.012 |
| Be | <.0002 | <.0002 | <.0002 | <.0002 | <.0002 |
| Cd | <.0075 | .0075 | <.0075 | <.0075 | <.0075 |
| Cr | <.0142 | <.0142 | <.0142 | <.0142 | <.0142 |
| Co | 0.008 | 0.007 | 0.009 | 0.005 | 0.006 |
| Cu | <0.0093 | <0.0093 | <0.0093 | <0.0093 | <0.0093 |
| Fe | 0.8961 | <0.0085 | <0.0085 | <0.0085 | <0.0085 |
| Pb | <0.02 | <0.02 | <0.02 | <0.02 | <0.02 |
| Mg | 35.250 | 0.524 | 0.738 | 0.873 | 2.621 |
| Mn | 1.387 | <0.0005 | <0.0005 | <0.0005 | <0.0005 |
| Ni | 0.070 | 0.038 | 0.041 | 0.044 | 0.051 |
| Se | <0.0112 | 0.0134 | <0.0112 | 0.0158 | <0.0112 |
| Ag | <0.0102 | <0.0102 | <0.0102 | <0.0102 | <0.0102 |
| Sr | 2.317 | 5.084 | 1.766 | 1.896 | 2.279 |
| Tl | <0.0748 | <0.0748 | <0.0748 | <0.0748 | 0.0864 |
| Sn | <0.1382 | 0.1411 | <0.1382 | 0.1912 | <0.1382 |
| V | <0.0134 | <0.0134 | <0.0134 | <0.0134 | <0.0134 |

TABLE 9

Metal content of acid mine drainage
after six hours of treatment with BDETNa$_2$.

| Element | Borehole Conc. 6 hr. (ppm) | 3" Pipe Conc. 6 hr. (ppm) | 4" Pipe Conc. 6 hr. (ppm) | Discharge Conc. 6 hr. (ppm) | Downstream conc. 6 hr. (ppm) |
|---|---|---|---|---|---|
| Al | 0.302 | 0.299 | 0.219 | 0.256 | 0.173 |
| Sb | 0.222 | 0.141 | 0.139 | 0.148 | 0.137 |
| As | <0.0118 | <0.0118 | <0.0118 | <0.0118 | <0.0118 |
| Ba | <.0031 | 0.017 | 0.006 | <.006 | 0.008 |
| Be | <.0002 | <.0002 | <.0002 | <.0002 | <.0002 |
| Cd | <.0075 | <.0075 | <.0075 | <.0075 | <.0075 |
| Cr | <.0142 | <.0142 | <.0142 | <.0142 | <.0142 |
| Co | 0.007 | 0.008 | 0.007 | 0.006 | 0.006 |
| Cu | <0.0093 | <0.0093 | <0.0093 | <0.0093 | <0.0093 |
| Fe | 0.0092 | <0.0085 | <0.0085 | <0.0085 | <0.0085 |
| Pb | <0.02 | <0.02 | <0.02 | <0.02 | <0.02 |
| Mg | 32.650 | 0.388 | 0.579 | 0.270 | 2.021 |
| Mn | 0.3509 | <0.0005 | <0.0005 | <0.0005 | <0.0005 |
| Ni | 0.060 | 0.046 | 0.032 | 0.046 | 0.034 |
| Se | <0.0112 | 0.0112 | <0.0112 | <0.0112 | <0.0112 |
| Ag | <0.0102 | <0.0102 | <0.0102 | <0.0102 | <0.0102 |
| Sr | 2.067 | 5.225 | 2.375 | 2.574 | 2.239 |
| Tl | 0.1077 | <0.0748 | <0.0748 | <0.0748 | <0.0748 |
| Sn | <0.1382 | 0.1385 | 0.2029 | 0.1510 | <0.1382 |
| V | <0.0134 | <0.0134 | <0.0134 | <0.0134 | <0.0134 |

TABLE 10

Metal Content of acid mine drainage
after 20 hours of treatment with BDETNa$_2$.

| Element | Borehole Conc. 20 hr. (ppm) | 3" Pipe Conc. 20 hr. (ppm) | 4" Pipe Conc. 20 hr. (ppm) | Discharge Conc. 20 hr. (ppm) | Downstream conc. 20 hr. (ppm) |
|---|---|---|---|---|---|
| Al | 0.283 | <0.0409 | 0.089 | 0.087 | 0.051 |
| Sb | 0.242 | 0.131 | 0.126 | 0.136 | 0.123 |
| As | <0.0118 | <0.0118 | <0.0118 | <0.0118 | <0.0118 |
| Ba | <.0031 | 0.010 | 0.004 | 0.004 | 0.006 |
| Be | <.0002 | <.0002 | <.0002 | <.0002 | <.0002 |
| Cd | <.0075 | <.0075 | <.0075 | <.0075 | <.0075 |
| Cr | <.0142 | <.0142 | 0.0101 | <.0142 | <.0142 |
| Co | 0.011 | 0.008 | 0.007 | 0.007 | 0.006 |
| Cu | <0.0093 | <0.0093 | <0.0093 | <0.0093 | <0.0093 |
| Fe | <0.0085 | <0.0085 | <0.0085 | <0.0085 | <0.0085 |
| Pb | <0.02 | <0.02 | <0.02 | <0.02 | <0.02 |
| Mg | 39.510 | 0.143 | 0.397 | <0.072 | 0.421 |
| Mn | 0.127 | <0.0005 | <0.0005 | <0.0005 | <0.0005 |
| Ni | 0.058 | 0.038 | 0.030 | 0.038 | 0.025 |
| Se | <0.0112 | <0.0112 | <0.0112 | <0.0112 | <0.0112 |
| Ag | <0.0102 | <0.0102 | <0.0102 | <0.0102 | <0.0102 |
| Sr | 2.104 | 4.019 | 1.949 | 2.131 | 1.803 |
| Tl | 0.1089 | <0.0748 | <0.0748 | <0.0748 | <0.0748 |
| Sn | <0.1382 | <0.1382 | <0.1382 | 0.1916 | <0.1382 |
| V | <0.0134 | <0.0134 | <0.0134 | <0.0134 | <0.0134 |

EXAMPLE 17

The ability of the 1,3 benzene metallate ligand synthesized as described in Example 6 was evaluated on soil samples containing known concentrations of Hg. Each soil sample was treated by admixing with ligand in a 1:1 molar ratio of ligand to Hg at least five times. Results are expressed as percent mercury immobilized by ligand. On average, over 98% of the Hg contained in soil samples was immobilized by the ligand (Table 11).

TABLE 11

Immobilization of mercury in soil using BDETNa$_2$ ligand.

| Sample ID | Initial Conc. of Hg prior to treatment (mg of Hg/g soil) | Final Conc. of Hg following treatment (mg of Hg/g soil) | % Hg Immobilized by BDETNa$_2$ |
|---|---|---|---|
| 1 | 10.223 | 0.296 | 97.10 |
| 2 | 10.106 | 0.115 | 98.86 |
| 3 | 9.859 | 0.042 | 99.57 |
| 4 | 10.783 | 0.115 | 98.93 |
| Mean | 10.243 | 0.142 | 98.62 |

Average Results: Based on a minimum of 5 treatments for each sample

EXAMPLE 18

An experiment was conducted to determine the effect of increasing the concentration of the 1,3 benzene metallate ligand of Example 6 to greater than a 1:1 molar ratio on ability of the ligand to bind Hg in soil. At an increase of 10% over a 1:1 ratio of ligand to metal, 93.06% of the Hg contained in the soil samples was immobilized (Table 12). Increasing the amount of ligand to 55% over a 1:1 molar ratio resulted in immobilization of 99.59% of the Hg contained in the soil samples.

TABLE 12

Immobiliztion of mercury in soil using increasing concentrations of disodium benzene thio ligand.

| Dosage increase from 1:1 molar (%) | Average Hg conc. not immobilized (mg Hg/g soil) | Average percent of Hg immobilized by BDETNa$_2$ |
|---|---|---|
| 10 | 0.711 | 93.06 |
| 20 | 0.451 | 95.60 |
| 25 | 0.309 | 96.99 |
| 30 | 0.214 | 97.91 |
| 40 | 0.138 | 98.65 |
| 45 | 0.115 | 98.88 |
| 50 | 0.110 | 98.93 |
| 55 | 0.042 | 99.59 |

The foregoing description of preferred embodiments of the invention has been presented for purposes of illustration and description. It is not intended to be exhaustive or to limit the invention to the precise form disclosed. Obvious modifications or variations are possible in light of the above teachings. The embodiments were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A chemical compound, comprising:

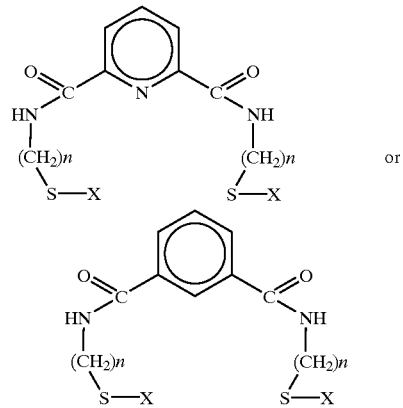

where n=1–4 and X is selected from the group consisting of hydrogen, lithium, sodium, potassium, rubidium, cesium, and francium.

2. A chemical compound, comprising:

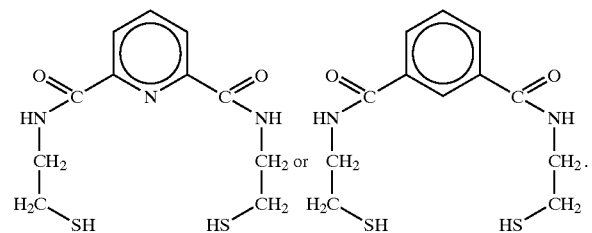

3. A chemical compound, comprising:

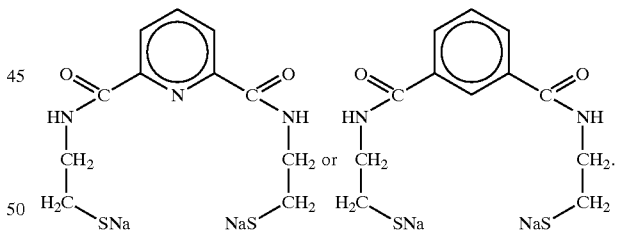

4. A method of removing metal from a starting material selected from the group consisting of a fluid, a solid, or any mixture thereof, comprising binding said metal in an effective amount of chelate ligand having a chemical formula:

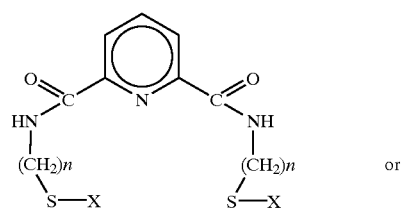

-continued

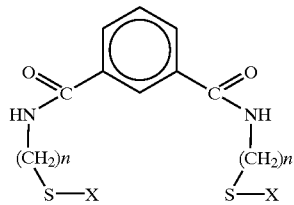

where n=1–4 and X is selected from the group consisting of hydrogen, lithium, sodium, potassium, rubidium, cesium, and francium.

5. The method of claim 4 wherein said metal bound with said chelate ligand may be any metal in or capable of being placed in a positive oxidation state.

6. The method of claim 4 wherein said metal bound with said chelate ligand is selected from a group consisting of lead, copper, mercury, cadmium, iron, nickel, zinc, aluminum, antimony, arsenic, barium, beryllium, chromium, cobalt, magnesium, manganese, selenium, silver, strontium, thallium, tin, gold, vanadium and mixtures thereof.

7. The method of claim 4 wherein said metal remains bound to said chelate ligands at pH values from about 0 to about 14.

8. A method of removing metal from a starting material selected from the group consisting of a fluid, a solid, or any mixture thereof, comprising binding said metal in an effective amount of a chelate ligand having a chemical formula:

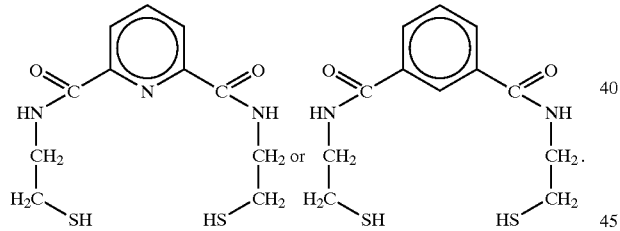

9. The method of claim 8 wherein said metal bound with said chelate ligand may be any metal in or capable of being placed in a positive oxidation state.

10. The method of claim 8 wherein said metal bound with said chelate ligand is selected from a group consisting of lead, copper, mercury, cadmium, iron, nickel, zinc, aluminum, antimony, arsenic, barium, beryllium, chromium, cobalt, magnesium, manganese, selenium, silver, strontium, thallium, tin, gold, vanadium and any mixtures thereof.

11. The method of claim 8 wherein said metal remains bound to said chelate ligands at pH values from about 0 to about 14.

12. A method of removing metal from a starting material selected from the group consisting of a fluid, a solid, or any mixture thereof, comprising binding said metal in an effective amount of a chelate ligand having a chemical formula:

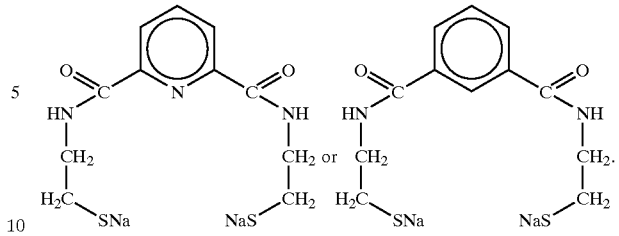

13. The method of claim 12 wherein said metal bound with said chelate ligand may be any metal in or capable of being placed in a positive oxidation state.

14. The method of claim 12 wherein said metal bound with said chelate ligand is selected from a group consisting of lead, copper, mercury, cadmium, iron, nickel, zinc, aluminum, antimony, arsenic, barium, beryllium, chromium, cobalt, magnesium, manganese, selenium, silver, strontium, thallium, tin, gold, vanadium and any mixtures thereof.

15. The method of claim 12 wherein said metal remains bound to said chelate ligands at pH values from about 0 to about 14.

16. A method of removing metal from water, comprising:
adding an effective amount of a soluble chelate ligand having a formula:

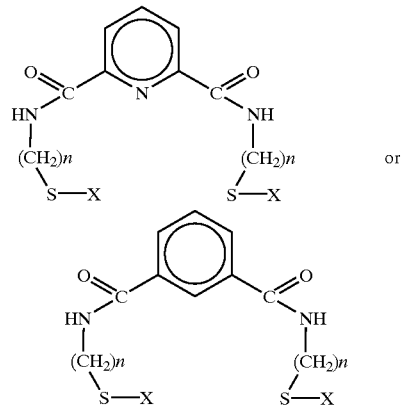

to the water to be treated, where n=1–4 and X is selected from the group consisting of hydrogen, lithium, sodium, potassium, rubidium, cesium, and francium;
binding said metal to be removed from said water to said chelate ligand; and
precipitating said chelate ligand bound to said metal from said water.

17. The method of claim 16 wherein said metal to be removed from said water may be any metal in or capable of being placed in a positive oxidation state.

18. The method of claim 16 wherein said metal to be removed from said water is selected from a group consisting of lead, copper, mercury, cadmium, iron, nickel, zinc, aluminum, antimony, arsenic, barium, beryllium, chromium, cobalt, magnesium, manganese, selenium, silver, strontium, thallium, tin, gold, vanadium and any mixtures thereof.

19. The method of claim 16 wherein said metal remains bound to said chelate ligands at pH values from about 0 to about 14.

20. A method of removal of metal from water, comprising:
adding an effective amount of a soluble chelate ligand having a formula:

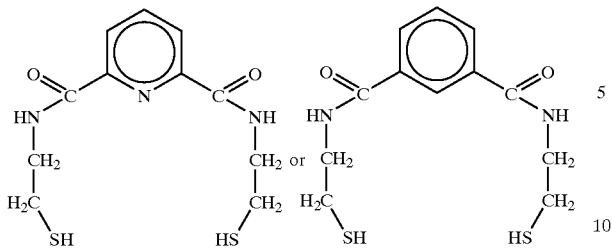

to the water to be treated;

binding said metal to be removed from said water to said chelate ligand; and precipitating said chelate ligand bound to said metal from said water.

21. The method of claim 20 wherein said metal to be removed from said water may be any metal in or capable of being placed in a positive oxidation state.

22. The method of claim 20 wherein said metal to be removed from said water is selected from a group consisting of lead, copper, mercury, cadmium, iron, nickel, zinc, aluminum, antimony, arsenic, barium, beryllium, chromium, cobalt, magnesium, manganese, selenium, silver, strontium, thallium, tin, gold, vanadium and any mixtures thereof.

23. The method of claim 20 wherein said metal remains bound to said chelate ligands at pH values from about 0 to about 14.

24. A method of removal of metal from water, comprising:

adding an effective amount of a soluble chelate ligand having a formula:

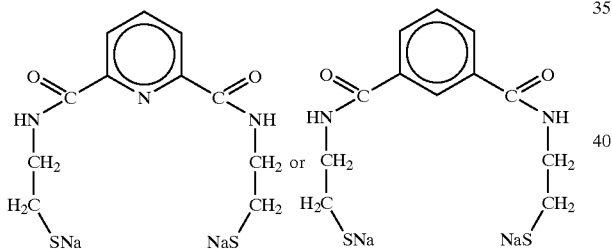

to the water to be treated;

binding said metal to be removed from said water to said chelate ligand; and precipitating said chelate ligand bound to said metal from said water.

25. The method of claim 24 wherein said metal to be removed from said water may be any metal in or capable of being placed in a positive oxidation state.

26. The method of claim 24 wherein said metal to be removed from said water is selected from a group consisting of lead, copper, mercury, cadmium, iron, nickel, zinc, aluminum, antimony, arsenic, barium, beryllium, chromium, cobalt, magnesium, manganese, selenium, silver, strontium, thallium, tin, gold, vanadium and any mixtures thereof.

27. The method of claim 24 wherein said metal remains bound to said chelate ligands at pH values from about 0 to about 14.

28. A method of acid mine drainage treatment, comprising:

adding an effective amount of a soluble chelate ligand having a formula:

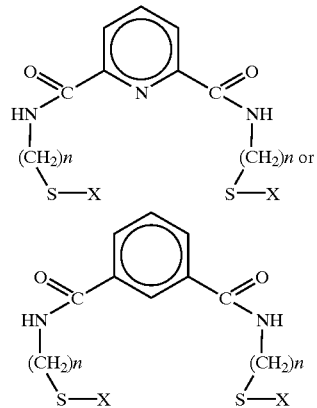

to the acid mine drainage to be treated, where $n=1-4$ and X is selected from the group consisting of hydrogen, lithium, sodium, potassium, rubidium, cesium, and francium;

binding a metal to be removed from said acid mine drainage to said chelate ligand; and precipitating said chelate ligand bound to said metal from said acid mine drainage.

29. The method of claim 28 wherein said metal to be removed from said acid mine drainage may be any metal in or capable of being placed in a positive oxidation state.

30. The method of claim 28 wherein said metal to be removed from said acid mine drainage is selected from a group consisting of lead, copper, mercury, cadmium, iron, nickel, zinc, aluminum, antimony, arsenic, barium, beryllium, chromium, cobalt, magnesium, manganese, selenium, silver, strontium, thallium, tin, gold, vanadium and any mixtures thereof.

31. The method of claim 28 wherein said metal remains bound to said chelate ligands at pH values from about 0 to about 14.

32. A method of acid mine drainage treatment, comprising:

adding an effective amount of a soluble chelate ligand having a formula:

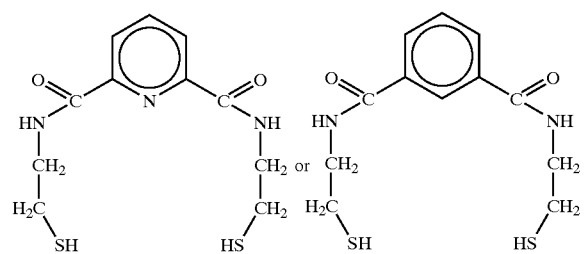

to the acid mine drainage to be treated;

binding a metal to be removed from said acid mine drainage to said chelate ligand; and precipitating said chelate ligand bound to said metal from said acid mine drainage.

33. The method of claim 32 wherein said metal to be removed from said acid mine drainage may be any metal in or capable of being placed in a positive oxidation state.

34. The method of claim 32 wherein said metal to be removed from said acid mine drainage is selected from a group consisting of lead, copper, mercury, cadmium, iron, nickel, zinc, aluminum, antimony, arsenic, barium, beryllium, chromium, cobalt, magnesium, manganese, selenium, silver, strontium, thallium, tin, gold, vanadium and any mixtures thereof.

35. The method of claim 32 wherein said metal remains bound to said chelate ligands at pH values from about 0 to about 14.

36. A method of acid mine drainage treatment, comprising:
adding an effective amount of a soluble chelate ligand having a formula:

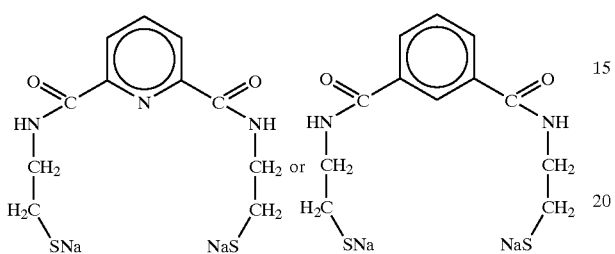

to the acid mine drainage to be treated;
binding a metal to be removed from said acid mine drainage to said chelate ligand; and
precipitating said chelate ligand bound to said metal from said acid mine drainage.

37. The method of claim 36 wherein said metal to be removed from said acid mine drainage may be any metal in or capable of being placed in a positive oxidation state.

38. The method of claim 36 wherein said metal to be removed from said acid mine drainage is selected from a group consisting of lead, copper, mercury, cadmium, iron, nickel, zinc, aluminum, antimony, arsenic, barium, beryllium, chromium, cobalt, magnesium, manganese, selenium, silver, strontium, thallium, tin, gold, vanadium and any mixtures thereof.

39. The method of claim 36 wherein said metal remains bound to said chelate ligands at pH values from about 0 to about 14.

40. A method of treatment of soil containing metal, comprising:
adding an effective amount of soluble chelate ligand having a formula:

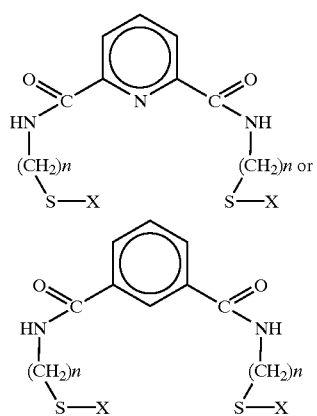

to the soil to be treated, where n=1–4 and X is selected from the group consisting of hydrogen, lithium, sodium, potassium, rubidium, cesium, and francium;
binding said metal in said soil to said chelate ligand; and
disposing of said soil containing said metal bound to said chelate ligands.

41. The method of claim 40 wherein said metal to be removed from said soil may be any metal in or capable of being placed in a positive oxidation state.

42. The method of claim 40 wherein said metal to be removed from said soil is selected from a group consisting of lead, copper, mercury, cadmium, iron, nickel, zinc, aluminum, antimony, arsenic, barium, beryllium, chromium, cobalt, magnesium, manganese, selenium, silver, strontium, thallium, tin, gold, vanadium and any mixtures thereof.

43. The method of claim 40 wherein said metal remains bound to said chelate ligands at pH values from about 0 to about 14.

44. A method of treatment of soil containing metal, comprising:
adding an effective amount of a soluble chelate ligand having a formula:

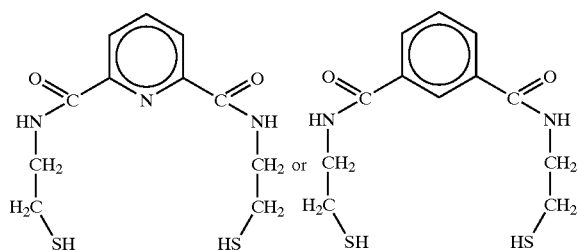

to the soil to be treated;
binding said metal in said soil to said chelate ligand; and
disposing of said soil containing said metal bound to said chelate ligands.

45. The method of claim 44 wherein said metal to be removed from said soil may be any metal in or capable of being placed in a positive oxidation state.

46. The method of claim 44 wherein said metal to be removed from said soil is selected from a group consisting of lead, copper, mercury, cadmium, iron, nickel, zinc, aluminum, antimony, arsenic, barium, beryllium, chromium, cobalt, magnesium, manganese, selenium, silver, strontium, thallium, tin, gold, vanadium and any mixtures thereof.

47. The method of claim 44 wherein said metal remains bound to said chelate ligands at pH values from about 0 to about 14.

48. A method of treatment of soil containing metal, comprising:
adding an effective amount of a soluble chelate ligand having a formula:

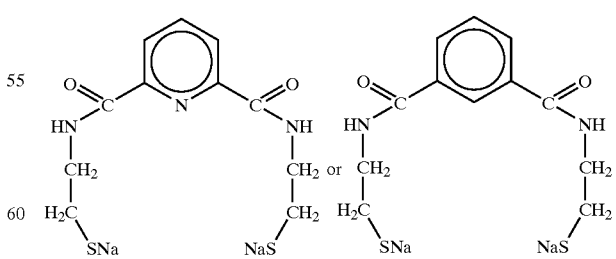

to the soil to be treated;
binding said metal in said soil to said chelate ligand; and
disposing of said soil containing said metal bound to said chelate ligands.

49. The method of claim 48 wherein said metal to be removed from said soil may be any metal in or capable of being placed in a positive oxidation state.

50. The method of claim 48 wherein said metal to be removed from said soil is selected from a group consisting of lead, copper, mercury, cadmium, iron, nickel, zinc, aluminum, antimony, arsenic, barium, beryllium, chromium, cobalt, magnesium, manganese, selenium, silver, strontium, thallium, tin, gold, vanadium and any mixtures thereof.

51. The method of claim 48 wherein said metal remains bound to said chelate ligands at pH values from about 0 to about 14.

* * * * *